United States Patent [19]

Robinson et al.

[11] Patent Number: 4,807,599
[45] Date of Patent: Feb. 28, 1989

[54] ILLUMINATING TONGUE DEPRESSOR

[75] Inventors: Herbert L. Robinson, Hoboken; Allen S. Epstein, Clifton, both of N.J.

[73] Assignee: Med-Struments, Inc., Totowa, N.J.

[21] Appl. No.: 47,645

[22] Filed: May 8, 1987

[51] Int. Cl.⁴ ............................ A61B 1/06; A61C 1/00
[52] U.S. Cl. ......................................... 128/16; 128/13; 433/29
[58] Field of Search ................ 128/11, 13, 15, 16, 128/18, 22, 6; 433/29; 362/32, 322, 120, 804, 9

[56] References Cited

U.S. PATENT DOCUMENTS

| | | | |
|---|---|---|---|
| 2,240,402 | 4/1941 | Joroslow | 128/16 |
| 2,247,258 | 6/1941 | Shepard | 128/16 |
| 2,723,661 | 11/1955 | Hall | 128/15 |
| 3,195,536 | 7/1965 | Hounanian et al. | 128/16 |
| 3,349,764 | 10/1967 | Edinger et al. | 128/16 |
| 3,734,084 | 5/1973 | Ousterhout | 128/15 |
| 3,890,960 | 6/1975 | Wansch, nee Kuhn et al. | 128/16 |
| 3,916,881 | 11/1975 | Heine | 128/16 |
| 4,320,745 | 3/1982 | Bhitiyakal et al. | 128/16 |
| 4,344,419 | 8/1982 | Burgin | 128/18 |
| 4,517,964 | 5/1985 | Upsher | 128/11 |
| 4,643,172 | 2/1987 | Taff et al. | 128/16 |

FOREIGN PATENT DOCUMENTS 1220633  3/1986  U.S.S.R. ............................ 128/15

*Primary Examiner*—Richard C. Pinkham
*Assistant Examiner*—Mark S. Graham
*Attorney, Agent, or Firm*—Samuelson & Jacob

[57] ABSTRACT

An illuminating tongue depressor includes a handle having a battery-operated light source and a depressor blade selectively coupled with or uncoupled from the handle for discard and replacement, the blade being constructed of a light-conducting synthetic resin material of relatively thin cross-section and being arched laterally to resist bending along the length thereof, the blade including a light-receiving surface at the proximal end thereof for juxtaposition with the light source and a light-directing configuration at the distal end thereof for directing light conducted from the light source and projected from the distal end to a defined area to be inspected during use of the tongue depressor in the examination of a patient.

13 Claims, 2 Drawing Sheets

ILLUMINATING TONGUE DEPRESSOR

The present invention relates generally to medical devices and pertains, more specifically, to a diagnostic spatula known more familiarly as a tongue depressor. In particular, the invention provides an improved tongue depressor which directs light to the area to be inspected for aiding such inspection and facilitating examination.

Tongue depressors have been in use routinely in the examination of patients for a very long time. Despite efforts to develop and manufacture tongue depressors of other materials, by far the most commonly used tongue depressors are those constructed of wood. Suggestions for substituting a synthetic resin material for wood have been made, but wood is still the preferred material, and large numbers of wooden tongue depressors are consumed annually. One suggestion for supplanting the wooden tongue depressor with a more effective diagnostic aid is a luminous spatula in which a spatula of light-conductive material is illuminated by a light source to assist in the examination of a patient. One such spatula is disclosed in U.S. Pat. No. 3,890,960 in which a light-conductive spatula is associated with a torch for receiving light from a lamp in the torch. The spatula includes a beaded stiffening configuration, and a luminous head on the spatula is provided with a top surface configuration which enables light to be refracted over the whole area of the top surface, as well as from the edges, for illumination of the cavity being examined.

The present invention combines the simplicity of a relatively thin tongue depressor having an overall configuration resembling familiar wooden tongue depressors, with the economy and convenience of a synthetic resin material, and the advantages of an illuminating feature for directing projected light to the particular area to be examined. Among the many objects and advantages provided by the present invention, the following are summarized: Effective illumination of the specific area being examined; one-hand operation to attain illuminated inspection of the particular area being examined; simplified construction in a familiar configuration easily employed in place of the commonly used wooden tongue depressor; exceptionally compact and highly portable for convenience of carrying, handling and use; ergonomic design facilitating handling and use; increased comfort for the patient being examined; ease of replacement and disposal of expended tongue depressor blades; and economy of manufacture in large numbers of consistent high quality.

The above objects and advantages, as well as further objects and advantages, are attained by the present invention which may be described briefly as an illuminating tongue depressor for directing light to a defined area to assist in the inspection of the defined area, the tongue depressor comprising: a handle; a depressor blade for use in conjunction with the handle during inspection of the defined area, the blade having a length extending longitudinally between a proximal end and a distal end and laterally between opposite sides, and including upper and lower surfaces defining a relatively thin blade thickness, a peripheral edge between the upper and lower surfaces, a root adjacent the proximal end of the blade, a tip at the distal end of the blade, and a light-conducting material between the upper and lower surfaces and extending along the blade from the root to at least a portion of the peripheral edge at the tip; a source of illumination including a light source associated with the handle and located so as to juxtapose the light source adjacent the root of the blade for transmitting light to the light-conducting material, which light-conducting material, in turn, will conduct the light at least to the portion of the peripheral edge at the tip of the blade; and a light-directing configuration extending along the portion of the peripheral edge at the tip of the blade for directing projected light from the portion of the peripheral edge at the tip of the blade toward the defined area. In one embodiment, the blade is arched in the lateral direction to resist bending along the longitudinal length thereof. In another embodiment, the light-directing configuration follows a graduated profile.

The invention will be understood more fully, while still further objects and advantages will become apparent, in the following detailed description of preferred embodiments illustrated in the accompanying drawing, in which.

Figures 1, 2, 3:
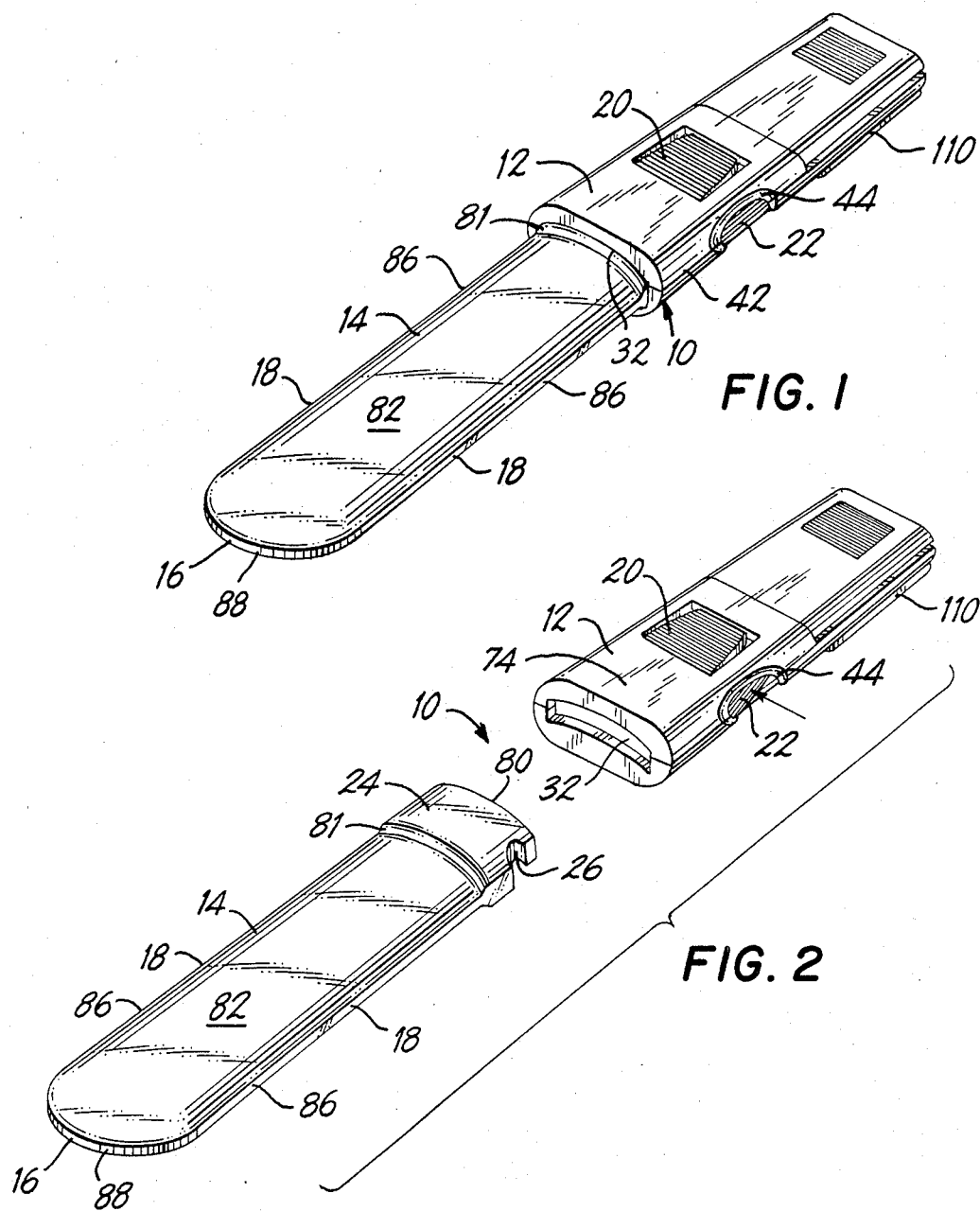
FIG. 1 is a perspective view of an illuminating tongue depressor constructed in accordance with the invention.
FIG. 2 is a perspective view similar to FIG. 1, but with the component parts detached.
FIG. 3 is a top longitudinal cross-sectional view of the tongue depressor showing internal components, including a light bulb and batteries.

Referring now to the drawing, and especially to FIG. 1 thereof, an illuminating tongue depressor constructed in accordance with the invention is illustrated at 10 and is seen to include a handle 12 and a depressor blade 14 projecting in a longitudinal direction from handle 12. Blade 14 has an overall configuration resembling the familiar wooden tongue depressors now in common use, having a generally rounded profile at tip 16 at the distal end thereof, generally straight parallel sides 18 and a uniform thickness along the length projecting beyond handle 12; however, blade 14 is constructed of a synthetic resin material, and preferably is molded from a clear acrylic, such as methyl methacrylate, so as to be capable of conducting light along the length of the blade 14. Blade 14 is secured at its proximal end within the handle 12 and a source of illumination is associated with the handle 12 and the proximal end of the blade 14, in a manner to be described more fully below, so as to provide light to be conducted to tip 16 and directed by tip 16 to project toward the particular area to be examined with the aid of the tongue depressor 10.

Tongue depressor 10 is utilized by grasping the handle 12 and placing the blade 14 in proximity with the particular area to be examined. Thus, blade 14 typically is inserted into the mouth of a patient and is manipulated to depress the tongue for inspection of the throat. Simultaneous with the grasping of handle 12, a button 20 on the handle 12 can be depressed to activate the source of illumination and transmit light to the tip 16 of the blade 14 where the light is projected into the throat to facilitate inspection. At the same time, some light is emitted from the sides 18 of the blade to assist in inspecting further surrounding areas, such as the buccal and palatine areas of the oral cavity.

In the illustrated preferred embodiments, blade 14 is selectively detachable from handle 12 so that an expended blade 14 can be discarded and replaced with a fresh blade 14. A release bar 22 in the handle 12 is actuated to release blade 14 which is then withdrawn from handle 12, as seen in FIG. 2. Blade 14 has a root 24 which includes a securing configuration having a notch 26 adjacent the proximal end of the blade 14, as will be explained in greater detail hereinafter. Suffice it to say that the construction and material of blade 14 is such that blade 14 is inexpensive enough to be manufactured economically in large numbers of consistent high quality and to be expendable after use.

Turning now to FIGS. 3 through 7, handle 12 includes a housing 30, preferably constructed of a molded synthetic resin, such as polystyrene. Housing 30 includes a socket 32 generally complementary to the root 24 of blade 14 for receiving the root 24 therein. A stop shoulder 34 at the base of the socket 32 is engaged by the proximal end of the blade 14 when root 24 is seated properly in socket 32.. At the same time, a latch 36 carried by release bar 22 enters notch 26 to secure the blade 14 in place. Release bar 22 is mounted for pivotal movement by means of a pin 38 which is integral with release bar 22 and extends into a journal 39 unitary with housing 30, release bar 22 being biased by a torsion spring 40 in a clockwise direction, as viewed in FIG. 3, so that latch 36 is biased by torsion spring 40 into notch 26. Actuation of release bar 22 to rotate the release bar 22 in a counter-clockwise direction, against the bias of torsion spring 40, will withdraw latch 36 from notch 26 and release blade 14 for withdrawal from the handle 12. Ejection of blade 14 from socket 32 is assisted by a helical spring 41 compressed upon insertion of blade 14 into socket 32. Helical spring 41 is centered laterally between the sides 18 of the blade 14 so that the blade 14 will not be cocked and tend to bind upon insertion into socket 32 or ejection from the socket 32. The effect of spring 41 is merely to assist in ejection and not to propel the blade 14 with any great force. Thus, blade 14 selectively is coupled with and uncoupled from handle 12 by means of movement of the release bar 22. Release bar 22 is located along a side edge 42 of housing 30 and straddles a recess 44 in the side edge 42 so that release bar 22 is placed properly for precluding inadvertent actuation during use of the tongue depressor 10 in the course of an examination, while facilitating deliberate actuation to release an expended blade 14 from handle 12.

A light source in the form of a light bulb 50, preferably a krypton bulb, is housed within a sleeve 52, which sleeve 52 serves as a heat sink for protecting the surrounding components from heat generated upon illumination of light bulb 50. Light bulb 50 is powered by batteries 54 contained within a battery compartment 56 in housing 30, the batteries 54 being connected in series, through a common contact 58. Light bulb 50 includes a first lead 60 connected to a first contact 62 which is in contact with a first battery terminal 64. A second lead 66 of light bulb 50 is connected to a second contact 68 which includes a leaf portion 70 juxtaposed with button 20 and overlapping a further contact 71 connected to a second battery terminal 72. Leaf portion 70 normally is spaced away from the further contact 71 above the further contact. Button 20 is a small cantilevered portion of the housing 30, and a hinge 73, preferably molded unitary with housing 30, enables swinging movement of the button 20 while biasing the button 20 into the upward position shown in FIG. 5. Upon depression of button 20 against the bias of hinge 73, leaf portion 70 of contact 68 is moved downwardly and engages further contact 71 to complete a circuit and illuminate light bulb 50. Button 20 is located along the top 74 of housing 30 for ease of actuation during the course of an examination. A battery compartment access door 76, latched at 78, enables access to the battery compartment 56 for removal and replacement of expended batteries 54.

Light bulb 50 is juxtaposed with the proximal end of the blade 14 so that light from the light bulb 50 is transmitted to the material of blade 14. As explained above, blade 14 is constructed of a light-conducting material, such as a clear acrylic, and the light transmitted to the root 24 of blade 14 is conducted longitudinally along the length of blade 14 to the distal end thereof. In order to enhance the transmission of light to blade 14, root 24 is made thicker than the remainder of blade 14, thereby providing a larger area along the rear surface 80 of root 24 for gathering a greater amount of light from light bulb 50, while maintaining a thinner, more economical and readily usable portion of blade 14 beyond root 24.

Figure 6:
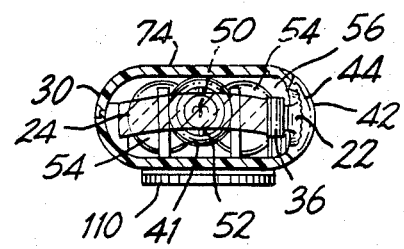
FIG. 6 is a lateral cross-sectional view taken along line 6—6 of FIG. 3.
Figure 5:
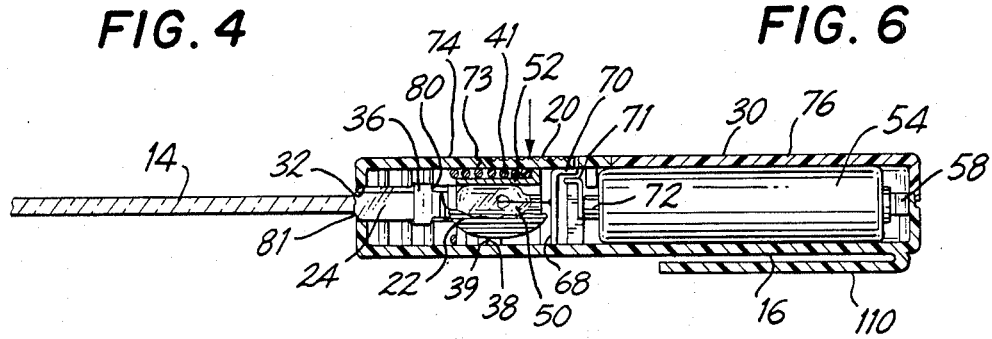
FIG. 5 is a side longitudinal cross-sectional view of the tongue depressor with the light bulb and batteries in place.
Figure 7:
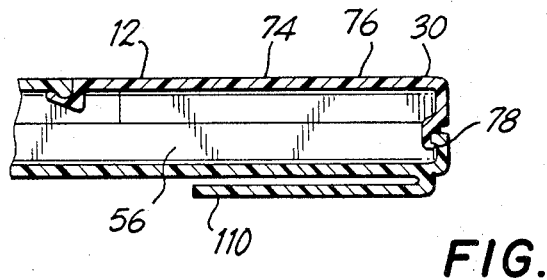
FIG. 7 is a fragmentary cross-sectional view with the batteries removed to show details of construction.

In view of the compact nature of handle 12, the intensity of the light available from bulb 50 and batteries 54 is limited. Yet it is important to direct the maximum amount of light available to the particular area to be inspected in connection with examination of a patient with tongue depressor 10. As set forth above, root 24 is made thicker in order to enable more light to be gathered at rear surface 80. Thus, as best seen in FIGS. 5 and 6, the height, or altitudinal extent, of rear surface 80 preferably is about the same as the diameter, or altitudinal extent, of light bulb 50. The transition between the thicker and thinner portions of blade 14 is made smooth and continuous, as shown at 81, so as to avoid loss of light along the transition. The light impinging on rear surface 80 will be conducted along the length of blade 14 to the distal end thereof. The upper surface 82 and the lower surface 84 of blade 14 preferably are made smooth and uninterrupted so as to enhance total internal reflection and minimize any loss of light through these surfaces. The peripheral edge 86, lying between upper and lower surfaces 82 and 84, and especially that portion 88 of the peripheral edge 86 located adjacent the tip 16, preferably is provided with a light-directing configuration which will direct light projected from the peripheral edge 86 to the defined area to be inspected. Some light is emitted at the peripheral edge 36 along sides 18, to assist in the inspection, as set forth above. In this manner, maximum use is made of the limited amount of light available as a result of the compact nature of the handle 12.

Figure 8:
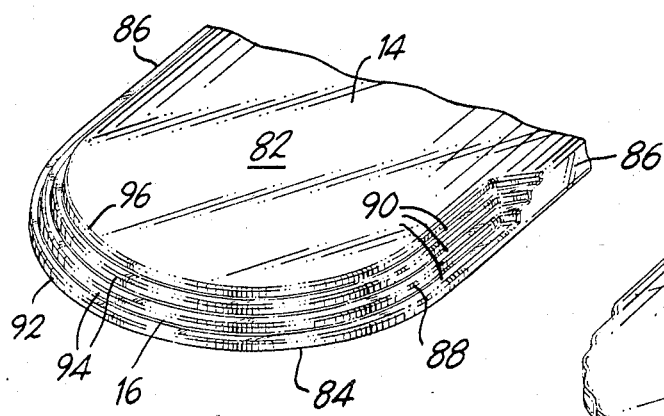
FIG. 8 is an enlarged perspective view of one tongue depressor tip configuration.
Figure 9:
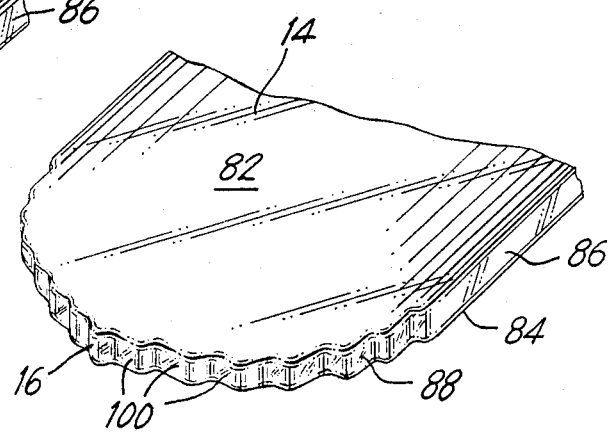
FIG. 9 is an enlarged perspective view of another tongue depressor tip configuration.

Accordingly, as seen in FIGS. 8 and 9, the tip 16 of blade 14 is provided with a graduated profile for effectively directing the light available at edge portion 88 of peripheral edge 86 so that the projected light will be concentrated and directed to the particular defined area to be illuminated for inspection. In the configuration of FIG. 8, the graduated profile includes a plurality of arcuate steps 90 proceeding upwardly from a largest radius step 92 at the lower surface 84 through consecutive steps 94 of decreasing radius to a smallest radius step 96 at the upper surface 82. All of the steps 90 extend along edge portion 88 of peripheral edge 86 and preferably have a lenticular cross-sectional shape in order to effect appropriate directing of the light projected into the areas to be inspected. In the configuration of FIG. 9, the graduated profile includes a plurality of steps 100 proceeding around the curved edge portion 88 of peripheral edge 86 at tip 16. Here, again, the steps 100 preferably have a lenticular configuration for light-directing purposes.

Figure 4:
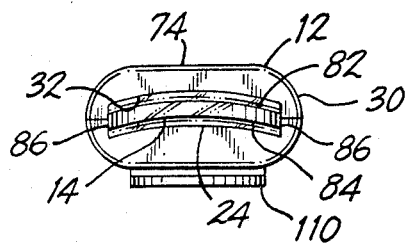
FIG. 4 is a front elevational view of the tongue depressor.

In order to provide blade 14 with sufficient rigidity along the length of the blade 14, without disturbing the smooth, uninterrupted surface characteristics needed to preclude light loss, the blade 14 is arched in the lateral direction. Thus, as best seen in FIGS. 4 and 6, upper surface 82 is convex and lower surface 84 is concave, and the cross-sectional configuration of blade 14 is curved, at least along the portion of the blade 14 between root 24 and top 16. In this manner, bending of the blade 14, during use, is resisted. The ability to maintain the blade 14 relatively thin conserves material and renders the blade 14 more economical to manufacture. In addition, the thin, smooth blade configuration enhances comfort of the patient. Further, the lateral curvature of blade 14 facilitates lateral manipulations of the blade 14 across the tongue of a patient during examination of the oral cavity. In addition, the arched configuration of the blade 14 along root 24 and the complementary socket 32 assures that blade 14 can be inserted into handle 12 only in the proper orientation, that is, with upper surface 82 facing upwardly and with lower surface 84 facing downwardly.

The entire tongue depresser 10 is very compact for ease of carrying, as well as ease of use. The handle 12 typically is about three inches long, just over one inch wide and about one-half inch thick. With blade 14 in place in the handle 12, the overall length of the entire device is less than eight inches. A pocket clip 110 on the housing 30 of handle 12 facilitates carrying the tongue depressor 10.

It will be seen that tongue depressor 10 combines the simplicity of a relatively thin tongue depressor having an overall configuration resembling familiar, ubiquitous wooden tongue depressors, with the economy, convenience and comfort of a synthetic resin tongue depressor, and the advantages of an illuminating feature which directs a maximum amount of light available in a compact device to the particular area to be examined.

It is to be understood that the above detailed description of embodiments of the invention is provided by way of example only. Various details of design and construction may be modified without departing from the true spirit and scope of the invention as set forth in the appended claims.

The embodiments of the invention in which an exclusive property or privilege is claimed are defined as follows:

1. An illuminating tongue depressor for directing light to a defined area to assist in the inspection of the defined area, the tongue depressor comprising:
    a handle;
    a depressor blade for use in conjunction with the handle during inspection of the defined area, the blade having a length extending longitudinally between a proximal end and a distal end and laterally between opposite sides, and including upper and lower surfaces, a peripheral edge between the upper and lower surfaces defining a relatively thin blade thickness, a root adjacent the proximal end of the blade, a tip at the distal end of the blade, and a light-conducting material between the upper and lower surfaces and extending along the blade from the root to at least a portion of the peripheral edge at the tip;
    a source of illumination including a light source associated with the handle and located so as to juxtapose the light source adjacent the root of the blade for transmitting light to the light-conducting material, which light-conducting material, in turn, will conduct the light at least to the portion of the peripheral edge at the tip of the blade; and
    a light-directing graduated profile configuration extending along the portion of the peripheral edge at the tip of the blade for directing projected light from the portion of the peripheral edge at the tip of the blade toward the defined area, the graduated profile configuration including a plurality of steps extending along the portion of the peripheral edge of the tip, the tip being rounded and each step being curved to extend along the rounded tip, the steps being arranged to diminish in radius from a step of larger radius adjacent the lower surface to a step of smaller radius adjacent the upper surface.

2. The invention of claim 1 wherein at least the portion of the blade between the root and the tip is arched in the lateral direction to resist bending along the longitudinal direction.

3. The invention of claim 1 wherein the blade is constructed of a light-conducting synthetic resin material.

4. The invention of claim 3 wherein at least the portion of the blade between the root and the tip is arched in the lateral direction to resist bending along the longitudinal length of the blade.

5. The invention of claim 3 wherein the root of the blade includes a light-receiving surface confronting the light source, the light source has a given altitudinal extent at the light-receiving surface, the thickness of the blade between the upper and lower surfaces at the light-receiving surface being greater than the thickness of the blade between the upper and lower surfaces at the tip such that the altitudinal extent of the light-receiving surface essentially matches the altitudinal extent of the light source.

6. The invention of claim 1 including coupling means for selectively coupling and uncoupling the blade and the handle.

7. The invention of claim 6 wherein:
    the coupling means includes a socket in the handle for receiving the root of the blade;
    the blade, including the root thereof, is arched in the lateral direction such that the upper surface is convex and the lower surface is concave; and
    the socket ia arched complementary to the root of the blade for receiving the root only in the orientation where the upper surface faces upwardly and the lower surface faces downwardly.

8. The invention of claim 1 wherein the steps have a lenticular configuration.

9. In an illuminating tongue depressor for directing light to a defined area to assist in the inspection of the defined area, the tongue depressor including a handle and a light source in the handle, the improvement comprising:
    a depressor blade for use in conjunction with the handle during inspection of the defined area, the blade having a length extending longitudinally between a proximal end and a distal end and laterally between opposite sides, and including upper and lower surfaces, a peripheral edge between the upper and lower surfaces, a root adjacent the proximal end of the blade, a tip at the distal end of the blade, and a lightconducting material between the upper and lower surfaces and extending along the blade from the root to at least a portion of the peripheral edge at the tip, and a light-directing graduated profile configuration extending along the portion of the peripheral edge at the tip of the blade for directing projected light from the portion of the peripheral edge at the tip of the blade toward the defined area, the graduated profile configuration including a plurality of steps extending along the portion of the peripheral edge at the tip, the tip being rounded and each step being curved to extend along the rounded tip, the steps being arranged to diminish in radius from a step of larger radius adjacent the lower surface to a step of smaller radius adjacent the upper surface.

10. The invention of claim 9 wherein the blade is constructed of a light-conducting synthetic resin material.

11. The invention of claim 9 wherein at least the portion of the blade between the root and the tip is arched in the lateral direction to resist bending along the longitudinal length of the blade.

12. The invention of claim 10 wherein the root of the blade includes a light-receiving surface confronting the light source, the light source has a given altitudinal extent at the light-receiving surface, the thickness of the blade between the upper and lower surfaces at the light-receiving surface being greater than the thickness of the blade between the upper and lower surfaces at the tip such that the altitudinal extent of the light-receiving surface essentially matches the altitudinal extent of the light source.

13. The invention of claim 9 wherein the steps have a lenticular configuration.

* * * * *